(12) United States Patent
Sandmore et al.

(10) Patent No.: US 8,978,657 B2
(45) Date of Patent: Mar. 17, 2015

(54) DUAL-LUMEN TRACHEAL TUBE WITH SHAPED LUMEN DIVIDER

(75) Inventors: Donald R. Sandmore, Lyons, CO (US); Jonathan Snyder, Northglenn, CO (US); Heather Harrison, Boulder, CO (US); Stanley Kaus, Longmont, CO (US); Mark Behlmaier, Erie, CO (US); Vida Keene, Longmont, CO (US)

(73) Assignee: Covidien LP, Mansfield, MA (US)

( * ) Notice: Subject to any disclaimer, the term of this patent is extended or adjusted under 35 U.S.C. 154(b) by 214 days.

(21) Appl. No.: 12/846,607

(22) Filed: Jul. 29, 2010

(65) Prior Publication Data

US 2012/0024292 A1 Feb. 2, 2012

(51) Int. Cl.
| | |
|---|---|
| A61M 16/04 | (2006.01) |
| A61M 16/00 | (2006.01) |
| A62B 9/06 | (2006.01) |
| A61M 25/00 | (2006.01) |

(52) U.S. Cl.
CPC ........... *A61M 16/04* (2013.01); *A61M 16/0404* (2014.02); *A61M 16/0431* (2014.02); *A61M 16/0459* (2014.02); *A61M 16/0486* (2014.02); *A61M 16/0488* (2013.01); *A61M 2025/0034* (2013.01); *A61M 2205/32* (2013.01); *A61M 2205/584* (2013.01)
USPC .................................................. 128/207.14

(58) Field of Classification Search
USPC ................ 601/6; 604/543, 284, 96.01, 101.1; 128/207.14, 207.15, 200.24, 200.26, 128/201.24, 202.27, 204.18, 911, 912, 128/207.16; 606/192, 194, 196
See application file for complete search history.

(56) References Cited

U.S. PATENT DOCUMENTS

| | | | |
|---|---|---|---|
| 3,964,488 A | 6/1976 | Ring et al. | |
| 4,233,984 A * | 11/1980 | Walling | 128/207.14 |
| 4,685,457 A | 8/1987 | Donenfeld | |
| 4,846,153 A | 7/1989 | Berci | |
| 4,949,716 A | 8/1990 | Chenoweth | |
| 4,982,729 A | 1/1991 | Wu | |
| 5,016,614 A | 5/1991 | MacAllister | |
| 5,038,766 A | 8/1991 | Parker | |
| 5,174,283 A | 12/1992 | Parker | |
| 5,203,320 A | 4/1993 | Augustine | |
| 5,245,992 A | 9/1993 | Nye | |
| 5,259,377 A | 11/1993 | Schroeder | |

(Continued)

FOREIGN PATENT DOCUMENTS

EP 2228090 A1 * 9/2010

OTHER PUBLICATIONS

Campos, Javier H. MD et al., Comparison of a Modified Double-Lumen Endotracheal Tube with a Single-Lumen Tube with Enclosed Bronchial Blocker, International Anesthesia Research Society, 1996, pp. 1268-1272, Issue 83.

(Continued)

*Primary Examiner* — Tan-Uyen (Jackie) T Ho
*Assistant Examiner* — Mark Wardas
(74) *Attorney, Agent, or Firm* — Fletcher Yoder PC

(57) ABSTRACT

Various embodiments of a tracheal tube having a shaped divider disposed therein for separation of a tracheal tube into multiple ventilation lumens are provided. In some embodiments, the divider divides a tracheal ventilation lumen from a bronchial ventilation lumen. In some embodiments, the shaped divider provides an irregular inner diameter that allows a relatively bulky device to be inserted into one or both lumens.

17 Claims, 6 Drawing Sheets

(56) References Cited

U.S. PATENT DOCUMENTS

| | | | |
|---|---|---|---|
| 5,309,906 A * | 5/1994 | LaBombard | 128/207.14 |
| 5,329,940 A | 7/1994 | Adair | |
| 5,333,608 A | 8/1994 | Cummins | |
| 5,339,805 A | 8/1994 | Parker | |
| 5,400,771 A | 3/1995 | Pirak et al. | |
| 5,429,127 A | 7/1995 | Kolobow | |
| 5,605,149 A * | 2/1997 | Warters | 128/207.14 |
| 5,607,386 A | 3/1997 | Flam | |
| 5,636,625 A | 6/1997 | Miyagi et al. | |
| 5,694,929 A | 12/1997 | Christopher | |
| 5,921,917 A | 7/1999 | Barthel et al. | |
| 5,954,636 A | 9/1999 | Schwartz et al. | |
| 5,964,217 A | 10/1999 | Christopher | |
| 6,142,144 A | 11/2000 | Pacey | |
| 6,189,533 B1 | 2/2001 | Simon et al. | |
| 6,196,225 B1 | 3/2001 | Allgeyer | |
| 6,312,374 B1 * | 11/2001 | von Hoffmann | 600/3 |
| 6,443,156 B1 | 9/2002 | Niklason et al. | |
| 6,520,183 B2 * | 2/2003 | Amar | 128/207.14 |
| 6,543,446 B1 | 4/2003 | Christopher | |
| 6,568,388 B2 | 5/2003 | Christopher | |
| 6,631,713 B1 | 10/2003 | Christopher | |
| 6,672,305 B2 | 1/2004 | Parker | |
| 6,849,042 B2 | 2/2005 | Christopher | |
| 6,860,264 B2 | 3/2005 | Christopher | |
| 6,923,176 B2 * | 8/2005 | Ranzinger | 128/200.26 |
| 6,929,600 B2 | 8/2005 | Hill | |
| 7,052,456 B2 | 5/2006 | Simon | |
| 7,921,847 B2 * | 4/2011 | Totz | 128/207.15 |
| 8,057,424 B2 * | 11/2011 | Patterson et al. | 604/43 |
| 2006/0025650 A1 | 2/2006 | Gavriely | |
| 2006/0253197 A1 | 11/2006 | NaPier | |
| 2008/0097350 A1 * | 4/2008 | Bell et al. | 604/266 |
| 2010/0030057 A1 | 2/2010 | Gavriely et al. | |
| 2010/0065569 A1 * | 3/2010 | Douglas | 220/288 |
| 2012/0024292 A1 | 2/2012 | Sandmore et al. | |
| 2012/0065569 A1 * | 3/2012 | Steegers et al. | 604/6.16 |
| 2012/0172664 A1 | 7/2012 | Hayman et al. | |
| 2012/0179009 A1 | 7/2012 | Gavriely | |
| 2012/0298111 A1 | 11/2012 | Wood et al. | |

OTHER PUBLICATIONS

Ayoub, CM et al., Advancing the Tracheal Tube Over a Flexible Fiberoptic Bronchoscope by a Sleeve Mounted on the Insertion Cord, Department of Anesthesiology, PubMed, Jan. 2003, pp. 1-4.

Mallinckrodt, Tyco Healthcare, Endobronchial Tubes, Jul. 2001.

* cited by examiner

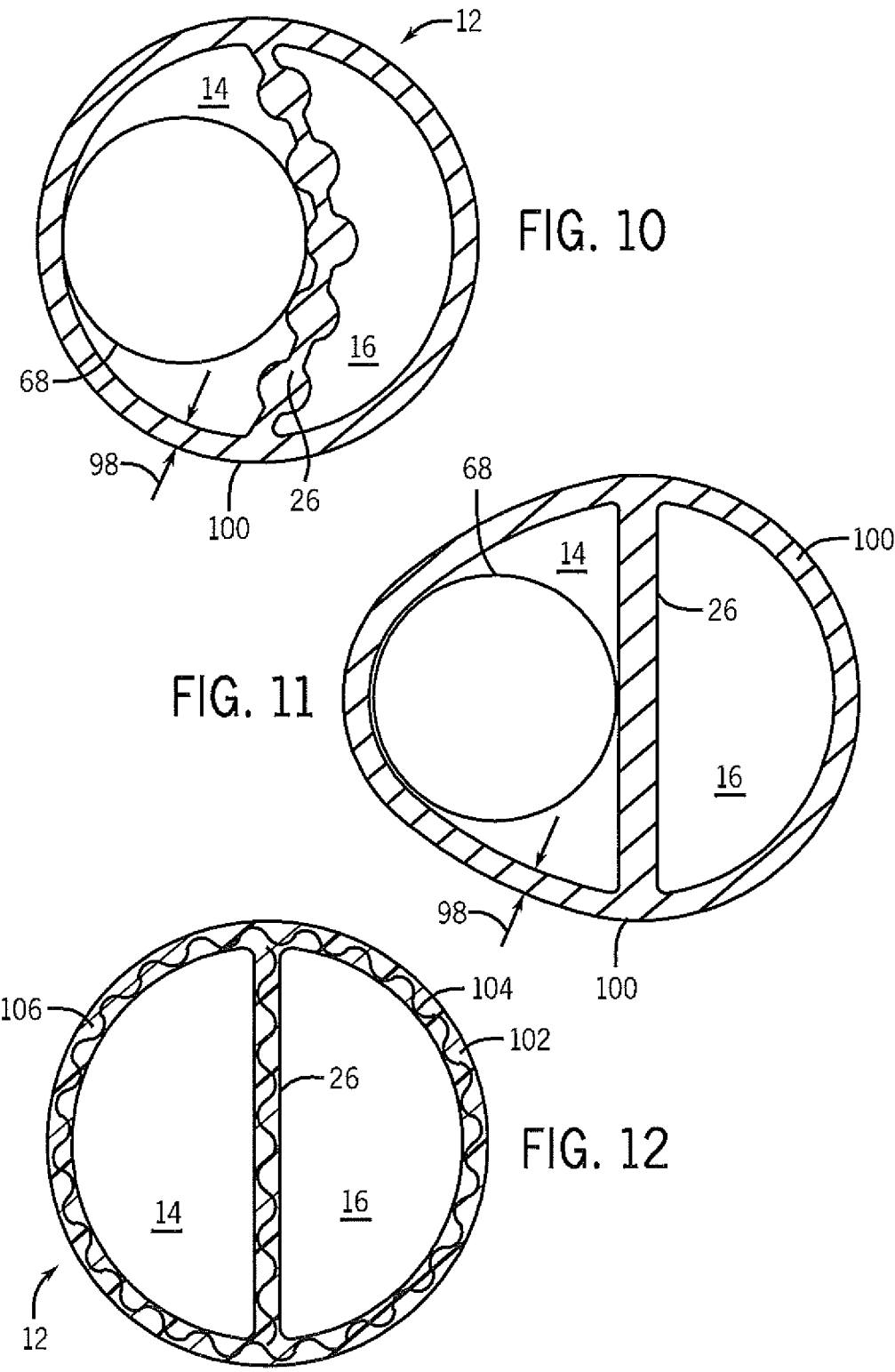

US 8,978,657 B2

DUAL-LUMEN TRACHEAL TUBE WITH SHAPED LUMEN DIVIDER

BACKGROUND

The present disclosure relates generally to medical devices and, more particularly, to dual-lumen tracheal tubes that may accommodate a viewing device, such as a bronchoscope.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into and out of the patient. For example, medical devices, such as tracheal tubes, may be used to control the flow of air or other gases through a trachea of a patient. Such tracheal tubes may include endotracheal tubes (ETTs), tracheostomy tubes, or transtracheal tubes. In many instances, it is desirable to provide a seal between the outside of the tube or device and the interior of the passage in which the tube or device is inserted, such as the trachea. In this way, substances can only flow through the passage via the tube or other medical device inserted in the tube, allowing a medical practitioner to maintain control over the type and amount of substances flowing into and out of the patient.

Depending on the clinical condition of the patient, a tracheal tube may be inserted that is capable of ventilating one lung or the other. For example, during thoracic surgery, surgeons may wish to isolate and perform surgery on an infected lung while simultaneously ventilating the healthy lung. Endobronchial tubes with dual lumens are typically used for this purpose. These tubes allow independent control of each lung through the separate lumens. One lumen may be blocked off to isolate the infected lung, while respiratory and anesthetic gases may be transferred through the other lumen. While endotracheal tubes involve correct tracheal placement, endobronchial tubes involve additional positioning within the correct bronchus. Such placement is often difficult and is mediated by bronchoscopes that are threaded through the bronchial lumen to visualize the surrounding tissue and determine if the bronchial lumen has been correctly positioned. However, bronchoscopes are bulky and difficult to operate within the relatively small diameter of the bronchial lumen.

BRIEF DESCRIPTION OF THE DRAWINGS

Advantages of the disclosed techniques may become apparent upon reading the following detailed description and upon reference to the drawings in which:

FIG. 10 is a cross-sectional view of the corrugated lumen divider of FIG. 9 in a stretched or expanded configuration;

FIG. 11 is a cross-sectional view of an alternative embodiment of an endobronchial tube with a rigid lumen divider with semi-rigid exterior walls; and FIG. 12 is a cross-sectional view of an alternative embodiment of an endobronchial tube with a thin, rigid lumen divider and exterior walls.

DETAILED DESCRIPTION OF SPECIFIC EMBODIMENTS

Figure 1:
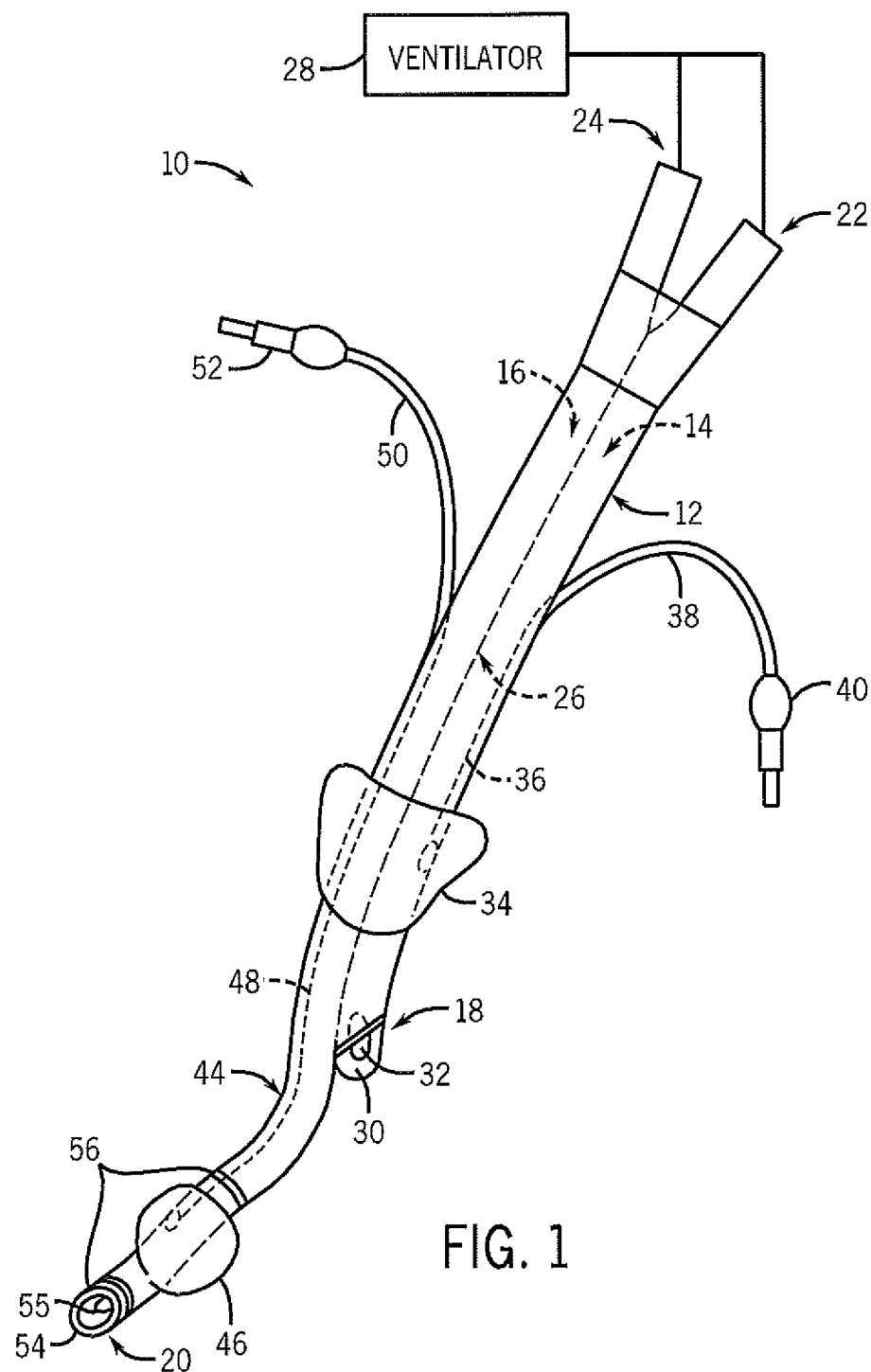
FIG. 1 is an elevational view of an endobronchial tube including a shaped lumen divider disposed therein in accordance with aspects of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of an endotracheal tube (ETT) having a shaped divider separating the tube into two lumens are provided herein. In a particular embodiment, the tracheal tube may be an endobronchial tube. Endobronchial tubes are double-lumen tracheal tubes that facilitate an airtight seal in the trachea and one stem of a patient bronchus to allow independent ventilation of one lung. Generally, an endobronchial tube includes two tubes of unequal length that are attached. One tube terminates within the tracheal airway space, i.e., the shorter tube has a distal end at a location similar to a typical endotracheal tube. The other, longer, tube is configured to extend past the shorter tube and into a left or right bronchial stem. Both tubes define a passageway for transferring gases to and from a patient.

While the total diameter of an endobronchial tube may be larger than that of a single lumen endotracheal tube, the diameter of each individual lumen of the endobronchial tube is relatively smaller than that of a single lumen endotracheal tube. Such a shift in diameter may be challenging for physicians during placement of an endobronchial tube. Because the endobronchial tube involves not only correct intubation within the trachea but also correct placement of the bronchial lumen with a left or right bronchial stem, physicians may use visualizing devices such as bronchoscopes to aid in the placement of the bronchial tube. However, commercial bronchoscopes are generally sized and shaped to be used in conjunction with the relatively larger lumen of a single-lumen endotracheal tube. As such, the bronchoscopes may not fit easily within either lumen of a double-lumen endobronchial tube. The shaped dividers as provided herein may allow clinicians to employ standard bronchoscopes with dual-lumen tubes, even bronchoscopes that may be sized and shaped to be used with relatively wider single-lumen endotracheal tubes. In particular embodiments, this may be advantageous for dual-lumen endobronchial tubes in smaller sizes, such as pediatric sizes, and may allow larger bronchoscopes to be used in conjunction with relatively small endobronchial tubes.

Provided herein are double-lumen tracheal tubes that incorporate a shaped dividing wall between the two lumens that is configured to accommodate bronchoscopes. The shaped divider may be curved or otherwise formed to allow the relatively bulky structure of a bronchoscope to pass without sacrificing a total volume within the lumens for transferring gas. In other embodiments, the shaped divider may be flexible or corrugated such that the divider may temporarily stretch and/or flex to accommodate the bronchoscope and may revert back to a default shape after the bronchoscope is removed. In yet other embodiments, the shaped divider may be formed from a rigid material while the outer walls of the lumen may be fanned from flexible materials that may stretch to accommodate a bronchoscope. Alternatively, the entire double-lumen tube may be formed from thin but rigid materials that allow a similar outer diameter relative to conventional endobronchial tubes, but that allow larger inner diameters.

The tracheal tubes as provided herein may be disposable rather than reusable, capable of conveying gas to and from the patient, and capable of providing separate ventilation channels to the tracheal space and to an individual lung. It should be noted that the provided tracheal tubes and methods of operating the tracheal tubes may be used in conjunction with auxiliary devices, such as airway accessories, ventilators, humidifiers, and so forth, which may cooperate with the tracheal tubes to maintain airflow to and from the lungs of the patient. For instance, the tracheal tubes may be placed in the trachea and coupled to a ventilator to protect the airway from possible obstruction or occlusion in emergency situations, such as when a patient experiences cardiac or respiratory arrest. For further example, the tracheal tubes may be coupled to an adapter or connector that is configured to cooperate with control circuitry to activate valving that controls the airflow to and from the patient during inspiration and expiration.

Furthermore, although the embodiments of the present disclosure illustrated and described herein are discussed in the context of endotracheal tubes such as endobronchial tubes, it should be noted that presently contemplated embodiments may include a shaped divider disposed within a main lumen associated with any of a variety of suitable airway devices. For example, the flexible membrane may be associated with a tracheostomy tube, a Broncho-Cath™ tube, a specialty tube, or any other airway device with a main ventilation lumen. Indeed, any device with a ventilation lumen designed for use in an airway of a patient may include a flexible membrane disposed therein to divide the main lumen into multiple chambers. Furthermore, as used herein, the term "tracheal tube" may include an endotracheal tube, a tracheostomy tube, a Broncho-Cath™ tube, a bronchoblocking tube, a specialty tube, or any other airway device. In addition, such shaped dividers may be incorporated into catheters or other inserted or implantable medical devices.

Turning now to the drawings, FIG. 1 is an elevational view of an exemplary endobronchial tracheal tube 10 configured to be placed in a patient bronchial stem in accordance with aspects of the present disclosure. The tracheal tube 10 includes a central tubular body 12 with a tracheal ventilation lumen 14 and a bronchial ventilation lumen 16. The tracheal lumen terminates at a tracheal lumen distal end 18 while the bronchial lumen terminates in a bronchial lumen distal end 20. Furthermore, the tracheal tube 10 may include a tracheal lumen proximal end 22 and a bronchial lumen proximal end 24. As shown, the tracheal ventilation lumen 14 and a bronchial ventilation lumen 16 may be attached to one another over a portion of the tubular body 12 and may separate at their respective proximal ends 22, 24 and distal ends 18, 20. Over the portion of the tubular body 12 in which the tracheal ventilation lumen 14 and a bronchial ventilation lumen 16 are attached, the tubular body 12 may include a shaped divider 26 that divides the tracheal ventilation lumen 14 and bronchial ventilation lumen 16 and serves as a shared wall between them.

The tracheal lumen proximal end 22 and a bronchial lumen proximal end 24 may be outfitted with separate connectors that may be attached to a ventilation device 28 during operation that may include a suitable controller (e.g., a processor-based control system) so that a clinician may direct airflow to and from both the tracheal ventilation lumen 14 and bronchial ventilation lumen 16. In other embodiments, either tracheal ventilation lumen 14 or the bronchial ventilation lumen 16 may be blocked or otherwise closed such that only one of the two lumens of the tracheal tube 10 is operational.

The tracheal lumen distal end 18 of ventilation lumen 14 terminates in an opening 30 and may be placed in a patient trachea during operation to maintain airflow to and from the patient's lungs. A Murphy's eye 32 may be located on the ventilation lumen 14 opposite the opening 30 to prevent airway occlusion when the tracheal tube assembly 10 is improperly placed within the patient's trachea. As illustrated, a tracheal cuff 34 may encircle the tubular body 12 and be inflated to seal against the walls of a body cavity (e.g., a trachea). The cuff 34 may be inflated via an inflation lumen 36 terminating in an inflation tube 38 connected to an inflation pilot balloon and valve assembly 40. Additionally, it should be noted that the cuff 34 may be any suitable cuff, such as a tapered cuff, a non-tapered cuff, and so forth. The tracheal ventilation lumen 14 may also include a suction lumen (not shown) that extends from a location on the tracheal tube 10 positioned outside the body when in use to a location on the tubular body 12 that terminates in a port located proximally to cuff 34 through which secretions may be aspirated. Bronchial ventilation lumen 16 is longer than tracheal ventilation lumen 14 and includes a distal portion 44 that extends past the tracheal lumen distal end 18. The bronchial ventilation lumen 16 may include a bronchial inflation cuff 46 that is configured to seal against the walls of a patient's bronchial stem. The cuff 46 may be inflated via an inflation lumen 48 terminating in an inflation tube 50 connected to an inflation pilot balloon and valve assembly 52, The tubular body 12, the cuff 34, and the shaped divider 26 may be formed from materials having desirable mechanical properties (e.g., puncture resistance, pin hole resistance, tensile strength, and so forth) and desirable chemical properties (e.g., biocompatibility). In addition, in one embodiment, the tubular body 12 and shaped divider 26 may be formed from the same material or different materials and may be manufactured as an integral unit, for example via an extrusion or co-extrusion process. In another embodiment, the shaped divider 26 may be adhered to or fastened to the tubular body 12 by any suitable process. For example, the connecting ends of the shaped divider 26 may be embedded in or adhered to tubular body 12. Further, in one embodiment, the walls of the cuff 34 or cuff 46 may be made of a polyurethane (e.g., Dow Pellethane® 2363-80A) having suitable mechanical and chemical properties. In other embodiments, the walls of the cuff 34 or cuff 46 may be made of silicone or a suitable polyvinyl chloride (PVC). In certain embodiments, the cuff 34 or cuff 46 may be generally sized and shaped as a high volume, low pressure cuff that may be designed to be inflated to pressures between about 15 cm H2O and 30 cm H2O. Further, bronchial cuff 46 may be a different color or include other identifying markings that allow a user to differentiate between the tracheal cuff 34 and the bronchial cuff 46. In addition, to assist in proper placement of the tube 10, x-ray visible markings 56 may be placed at any appropriate location. For example, the markings 56 may outline a bronchial distal opening 54 or a side eye 55.

Figure 2:
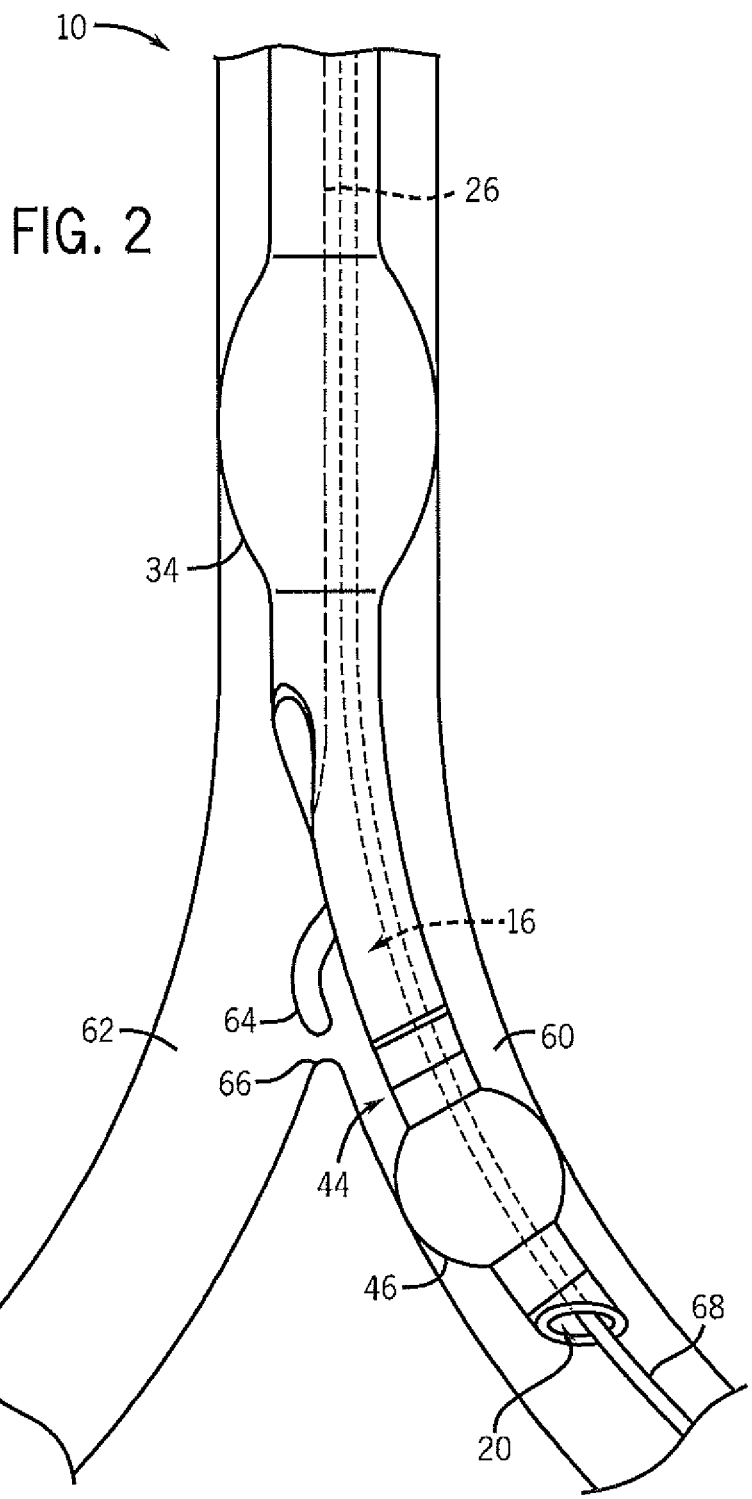
FIG. 2 is a perspective view of an exemplary endobronchial tube positioned within the left bronchus of a patient.

During operation, an endobronchial tube 10 is inserted into the trachea of a patient and positioned within the left or right bronchial stem and the tracheal cuff 34 and bronchial cuff 46 are inflated to isolate the appropriate airway structures. In certain embodiments, a tracheal tube 10 may be configured to be positioned within a left bronchial stem 60, as shown in FIG. 2. In such an embodiment, the tube 10 may have particular features that assist is positioning the distal portion 44 and the bronchial cuff 46. For example, relative to the right bronchial stem 62, the left bronchial stem is relatively curved. Accordingly, the distal portion 44 may be curved in a similar manner. Further, the tube 10 may include a protrusion 64 to help position the tube 10 relative to the patient's carina 66. After insertion, a bronchoscope 68 may be threaded into the bronchial ventilation lumen 16 to visualize the tissue surrounding the tissue surrounding the bronchial distal end 20 to determine if the tube 10 has been properly positioned.

Figure 3:
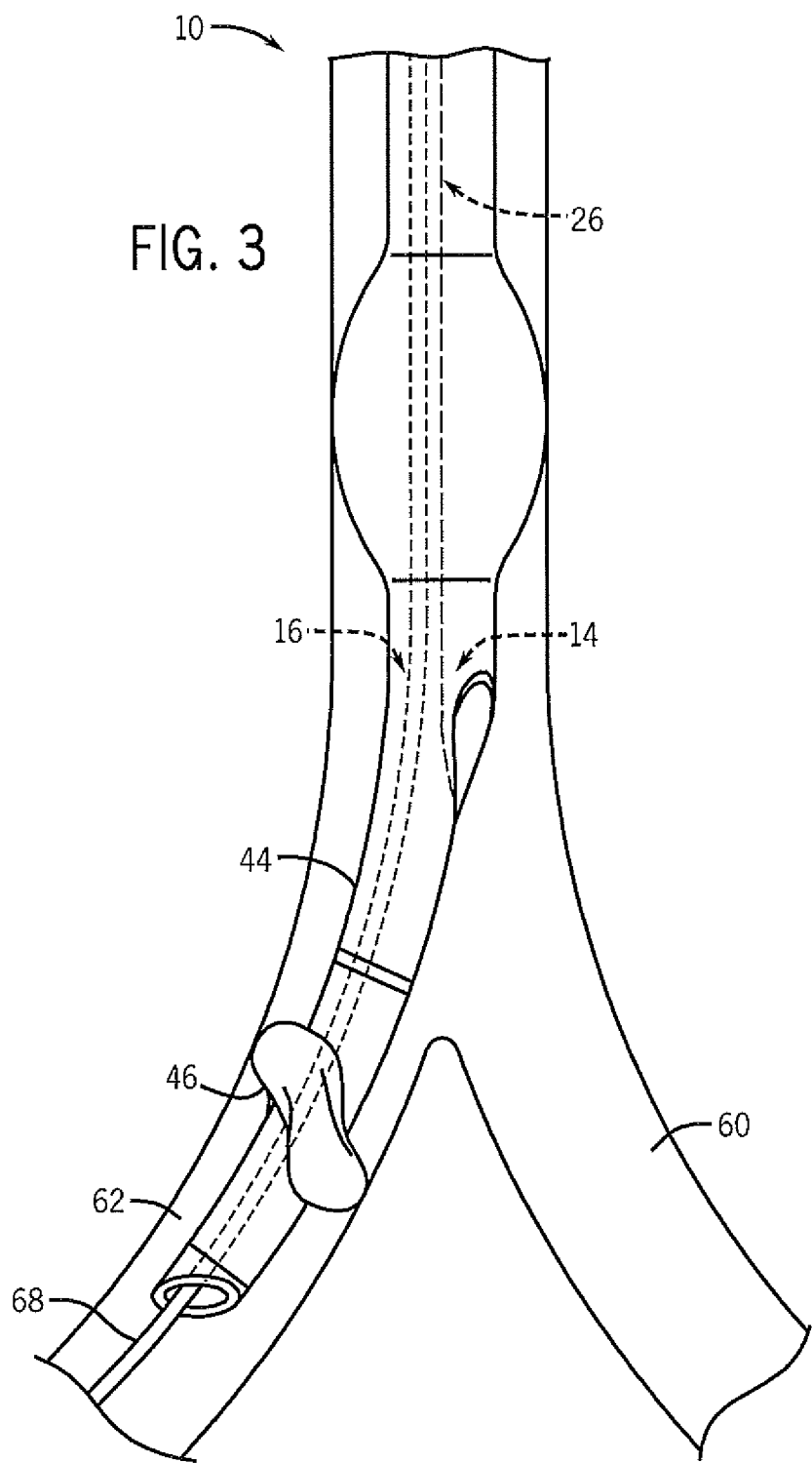
FIG. 3 is a perspective view of an exemplary endobronchial tube positioned within the right bronchus of a patient.

FIG. 3 illustrates a tracheal tube 10 that is configured to be positioned within a right bronchial stem 62. Because the right stem is relatively straighter than the left bronchial stem 60, the distal portion 44 of the tube 10 may have less of a curve. In addition, the bronchial cuff 46 may be shaped, for example with an S-shape, to provide an improved seal. Regardless of whether the tube 10 is right stem or left stem-specific, the shaped divider 26 is adapted to accommodate bronchoscope 68, e.g., by providing a larger diameter within the bronchial ventilation lumen 16, or by providing an irregularly-shaped space that better accommodates the bronchoscope 68. It should be understood that any configuration of the shaped divider 26 that influences the shape and/or inner diameter of bronchial ventilation lumen 16 may also have a corresponding effect on the tracheal ventilation lumen 14, because the shaped divider 26 serves as a partition or wall between these lumens along the portion of the tube 10 where they are joined.

Figure 4:
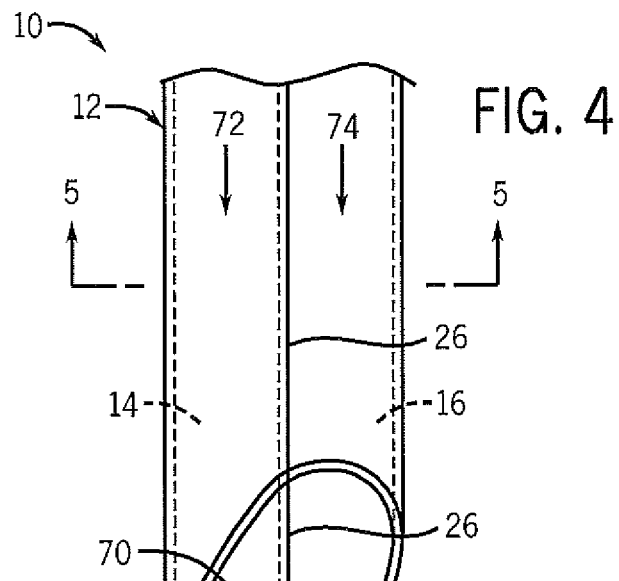
FIG. 4 is an elevational view of a portion of an exemplary endobronchial tube.

FIG. 4 is an elevation view of a portion of an exemplary endobronchial tracheal tube 10 with a shaped divider 26. The shaped divider 26 forms a portion of the interior wall of the tracheal ventilation lumen 14 and the bronchial ventilation lumen 16. As shown, the tracheal ventilation lumen 14 terminates in opening 30. At opening 30, the shaped divider transitions from an interior wall divider to an exterior wall 70. That is, where the tracheal ventilation lumen 14 and the bronchial ventilation lumen 16 are attached, the shaped divider 26 is entirely within the tubular body 12. However, in the distal portion 44 of the bronchial ventilation lumen 16, the shaped divider 26 extends out of opening 30 such that the shaped divider forms a portion of the exterior wall 70 of the bronchial ventilation lumen 16. The exemplar), transition of the shaped divider 26 from an interior element to an exterior wall 70 is illustrated in the cross sections take along lines 5-5 and 6-6 of FIG. 4. In embodiments in which the exterior wall 70 of the distal portion 44 is formed in part from the shaped divider 26, the shaped divider 26 is sufficiently rigid to hold the distal portion 44 in its desired shape and allow the distal portion 44 to be threaded into the correct bronchial stem.

Figure 5:
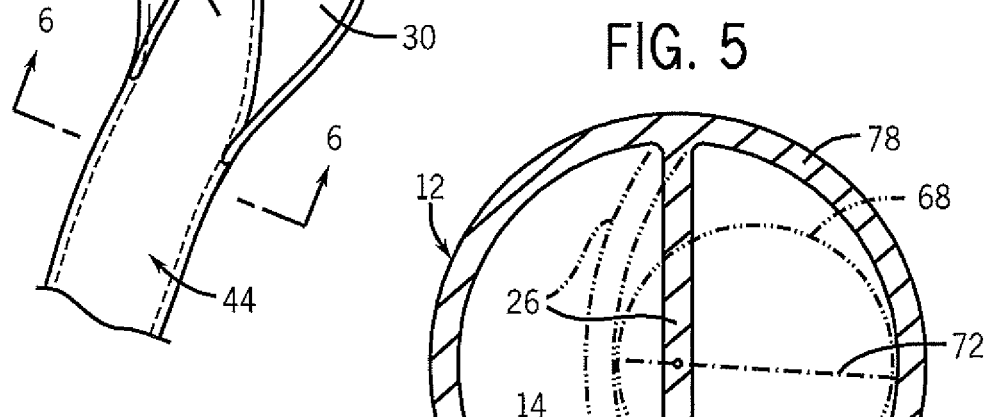
FIG. 5 is an exemplary cross sectional view through a section of the endobronchial tube of FIG. 4.
Figure 6:
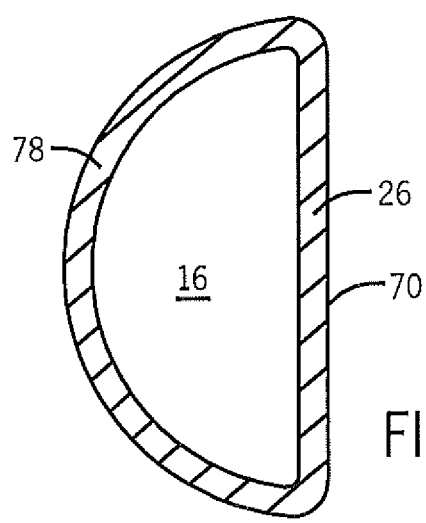
FIG. 6 is an exemplary cross sectional view through a section of the endobronchial tube of FIG. 4.

For example, FIG. 5 illustrates a section of tubular body 12 taken along line 5-5 of FIG. 4, which is generally orthogonal to the airflow axes 72 and 74 (see FIG. 4) of the tubular body 12. At this position along the tubular body 12, the shaped divider 26 is configured to divide the tubular body 12 and to provide an airtight divider between the tracheal ventilation lumen 14 and the bronchial ventilation lumen 16. As shown, the shaped divider 26 bisects or forms a continuous structure than connects two points on annulus 78, which forms an exterior wall of tubular body 12 at line 5-5. In the depicted embodiment, the shaped divider 26 may be flexible or elastomeric so that one or both of the ventilation lumens is able to accommodate a device, such as a bronchoscope 68. As shown, the bronchoscope 68 has a diameter 72 that is larger than the largest width of either the tracheal ventilation lumen 14 or bronchial ventilation lumen 16 when the shaped divider 26 is in a resting, unstretched state. When the bronchoscope 68 is threaded into the bronchial ventilation lumen 16, the shaped divider 26 stretches to accommodate the width of the diameter 72 of the device. FIG. 6 illustrates a section of tubular body 12 taken along line 6-6 of FIG. 4, which is generally orthogonal to the airflow axis 74 of the bronchial ventilation lumen 16. FIG. 6 illustrates the distal portion 44 of the bronchial ventilation lumen 16, which is distally located relative to opening 30. Here, portions of the tracheal ventilation lumen 14 have been removed from annulus 78 such that only the bronchial ventilation lumen 16 remains. Accordingly, the exterior side wall 70 in the distal portion 44 is a combination of a section of annulus 78 (e.g., a semicircular section) and the shaped divider 26. As shown, the bronchial ventilation lumen is generally D-shaped. However, the distal portion 44 of the bronchial ventilation lumen 14 may be reshaped to form a more annular structure, e.g., via heat shaping. In addition, any nonlinearity of the distal portion walls that is the result of nonlinearity in the shaped divider 26 may be smoothed during a reshaping process.

Figure 7:
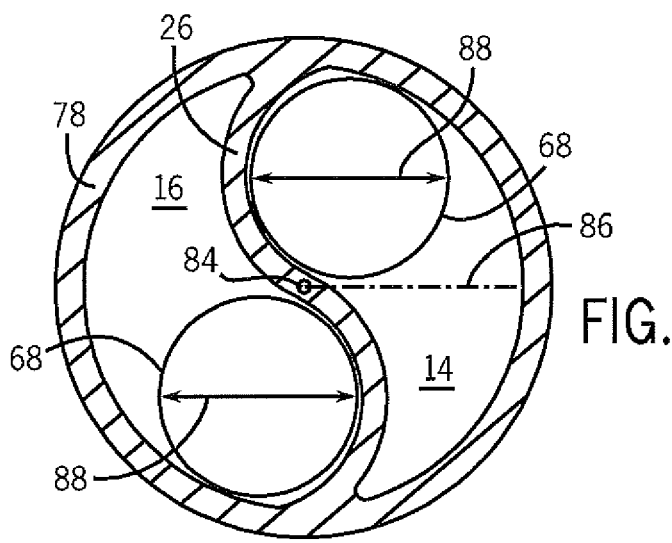
FIG. 7 is an exemplary cross sectional view of an embodiment of an endobronchial tube with an S-shaped lumen divider.

FIG. 7 is a cross-sectional view of an exemplary tracheal tube 10 in which the shaped divider 26 forms a non-axial (e.g., not forming a straight line) S-shaped structure. In certain embodiments, the shaped divider 26 may be generally rigid and inelastic, which may add rigidity to the distal portion 44 of the tracheal tube 10 for ease of insertion into a patient. The S-shaped shaped divider 26 may divide the tube into two equal volume sections at the cross-section. That is, although in the depicted embodiment the shaped divider 26 is non-linear or non-axial, the shaped divider 26 is configured within the tubular body 12 such that the cross-sectional volume of the bronchial ventilation lumen 16 and the tracheal ventilation lumen 14 are approximately equal. As shown, the annulus 78 formed by the cross section has a midpoint 84 and a radius 86. The shaped divider 26 may divide the annulus 78 such that lumens 14 and 16 may accommodate a generally circular volume having a diameter 88, which may be wider than the radius 86, depending on the curvature of the shaped divider 26. Alternatively, the irregular shape may enhance the flexibility of the shaped divider 26. In this manner, a dual-lumen tube may accommodate a bronchoscope 68 that would be too wide to fit into a lumen simply bisected into two semicircular regions (i.e., D-shaped regions) of equal volume. That is, the irregular shape of the shaped divider 26 may create certain wider regions of the lumens 14 and 16 such that the bronchoscope 68 may be more easily threaded into tubular body 12.

The outer diameter of the tubular body 12 of the tracheal tube 10 may be any suitable size for insertion into a patient. In one embodiment, the outer diameter may be about 9 mm to about 14 mm. Further, the widest inner diameter of the tracheal ventilation lumen 14 and the bronchial ventilation lumen may be between about 3 mm and about 6 mm. However, in particular embodiments, depending on the configuration of the shaped divider 26, a tracheal tube 10 may have widest inner diameters of at least 4 mm or widest inner volumes in each of the two lumens 14 and 16 to accommodate a standard fiberoptic bronchoscope.

Figure 8:
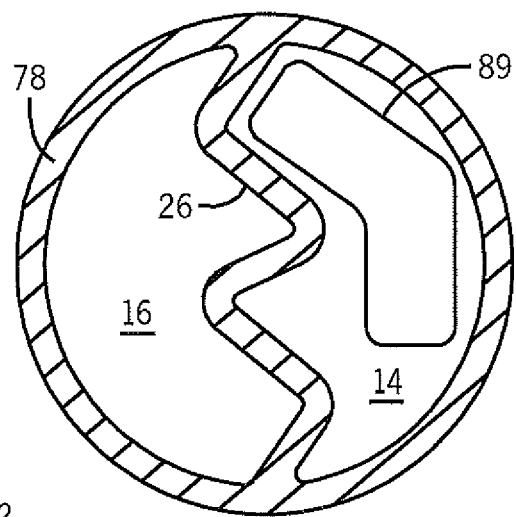
FIG. 8 is a cross-sectional view of an alternative embodiment of an endobronchial tube with a zigzag lumen divider.

It should be understood that the shaped divider 26 may be formed in any shape, elastic or inelastic, that accommodates an inserted device or that forms at least one lumen of an appropriate volume for gas transfer. For example, in an alternative embodiment, shown in FIG. 8, a cross sectional view of an exemplary tracheal tube 10, the shaped divider 26 may have a substantially zigzag shape. The shape of the divider 26 may be selected to accommodate an inserted medical device with a particular cross-sectional profile. For example, as shown, a device 89 may have an L-shaped profile that may fit within a zigzag shape. In other embodiments, the shaped divider may be Z-shaped, curvilinear, or hyperbolic. In some embodiments the shaped divider 26 may divide the tubular body 12 into two lumens of equal volume, while in other embodiments, the shaped divider 26 may divide the tubular body 12 into two or more lumens of unequal volume. For example, it is envisioned that a shaped divider 26 as provided herein may be incorporated into an endotracheal tube with a single lumen for gas transfer and surrounding smaller lumens, such as lumens for suction of secretions.

Figure 9:
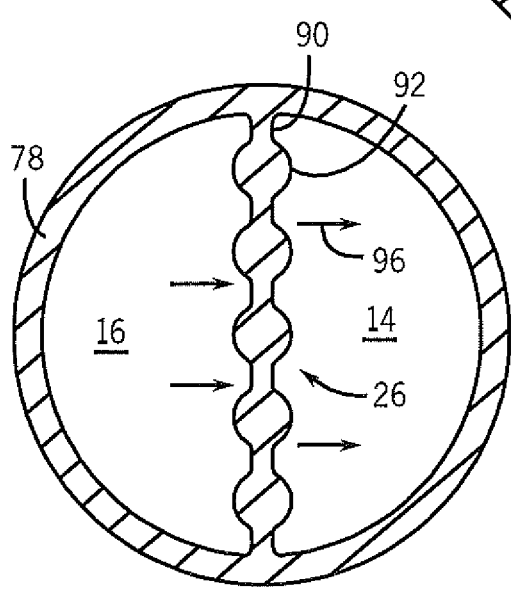
FIG. 9 is a cross-sectional view of an alternative embodiment of an endobronchial tube with a corrugated lumen divider.

Further, the shaped divider 26 may be formed all or in part from flexible or elastic materials that may change their shape upon experiencing a biasing force. For example, as shown in FIG. 9, a cross sectional view of an exemplary tracheal tube 10, a shaped divider 26 may be formed in a generally corrugated shape. That is, certain portions of the shaped divider 26 may be relatively rigid and inelastic longitudinal (e.g., running along the axis of the airflow) thick pieces 92 that are interconnected by longitudinal thin-walled elastomeric pieces 90. When a bronchoscope or other rigid device is threaded into either ventilation lumen, for example bronchial lumen 16, the force of the threading may cause the thin-walled portions 90 to stretch in direction 96 to accommodate the bronchoscope, as shown in FIG. 10.

Such a configuration provides rigidity to the shaped divider 26, which allows the distal portion 44 to hold its shape, while also providing a mechanism for a temporary change in internal diameter for both the tracheal ventilation lumen 14 and the bronchial ventilation lumen 16. In addition, the corrugated configuration may be formed integrally with the tubular body 12 by extruding portions of a single material (e.g., the same material used to form the exterior annulus 78 of the tubular body 12) at different thicknesses. In this manner, a flexible shaped divider 26 may be provided without the addition of complex manufacturing steps or materials. Further, an embodiment of the shaped divider 26 may include any combination, shape, and number of the thin-walled pieces 90 and the thick pieces 92.

In additional embodiments, the shaped divider 26 may be a flexible or elastomeric membrane that is connected (e.g., embedded in the exterior walls or adhered) at two points along the annulus 78 such the shaped divider 26 divides the annulus 78 into two equal-volume lumens. In such embodiments, the elastomeric shaped divider 26 may still be relatively stiff. For example, the shaped divider 26 may be formed from elastic materials of sufficient thickness to hold the shape of the distal portion 44 while also expanding if a medical device slightly larger than the inner diameter is threaded into the lumen. For example, the shaped divider may stretch to temporarily create an inner diameter in one lumen that is at least 4mm.

Because the shaped divider 26 forms a portion of the exterior wall of the distal portion 44, the stiffness of the shaped divider 26 contributes to the overall rigidity of the tracheal tube 10. In one embodiment, if the shaped divider 26 is sufficiently stiff, e.g., in one embodiment, if the shaped divider 26 is at least 65-70 Shore A, other portions of the tubular body 12 may be more flexible or conformable. For example, FIG. 11 illustrates a cross-section of an exemplary tube 10 in which the shaped divider 26 is rigid and the exterior walls 100 of the tube 10, forming the exterior walls of the tracheal ventilation lumen 14 and the bronchial ventilation lumen 16, are thin and conformable. In one embodiment, the exterior walls may stretch or expand to accommodate a medical device 68. In other embodiments, the thin exterior walls 100 may be generally inelastic. However, because of their thickness 98 relative to thicker tracheal tube walls, the cross-sectional area of each lumen 14 and 16 may be slightly larger. In one embodiment, the shaped divider 26 and the exterior walls 100 are formed from the same material, but the shaped divider 26 is at least twice as thick as the walls 100. In another embodiment, the shaped divider 26 is at least 1mm in thickness and the walls 100 have a thickness 98 of less than 0.5mm or less than 0.1mm.

While the preceding embodiments have related to shaped dividers 26 of sufficient stiffness to allow the distal portion 44 to be threaded into a bronchial stem, it is envisioned that the tubular body 12 may be formed from a thin but rigid material. Such a material may that provides the desired outer diameter for the patient along with increased inner diameters of the tracheal ventilation lumen 14 and bronchial ventilation lumen 16. FIG. 12 is an embodiment of a tracheal tube 10 in which the tubular body 12, including shaped divider 26, is formed from a polymer 102 that has been extruded with a rigid polymer web 104 or a rigid filler or extruded over a rigid framework, such as a nylon wire mesh. It is envisioned that thin, rigid materials may allow the shaped divider 26 and tube walls 106 to be less than about 0.5 mm, 0.25 mm, or 0.1mm in thickness. By reducing the thickness of the shaped divider 26 and tube walls 106, the inner diameter of each lumen 14 and 16 may increase by 1mm or more.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube, comprising:
   a side wall;
   a first ventilation lumen having a first distal end and a first proximal end;
   a second ventilation lumen adjacent to the first lumen, the second ventilation lumen having a second distal end and a second proximal end; and
   a flexible divider coupled to the side wall, the flexible divider dividing the first ventilation lumen from the second ventilation lumen and forming a portion of an exterior wall of the second ventilation lumen at a location distal to the first distal end of the first ventilation lumen and wherein the flexible divider extends to the second distal end, wherein the first ventilation lumen and the second ventilation lumen have substantially equal cross-sectional areas, and wherein the flexible divider comprises alternating inelastic thick portions and elastomeric thin portions, and wherein the flexible divider has rigid and non-planar side surfaces to create at least one enlarged region for passage of a medical device through the enlarged region.

2. The tracheal tube of claim 1, wherein the tracheal tube is configured to be coupled to at least one of a ventilator, a bag for ventilation, inspiration valving, expiration valving, or an air supply.

3. The tracheal tube of claim 1, comprising a first cuff disposed around the first ventilation lumen and the ventilation second lumen, and a second cuff disposed around only the second ventilation lumen.

4. The tracheal tube of claim 3, wherein the first distal end is located on the tracheal tube between the first cuff and the second cuff.

5. The tracheal tube of claim 1, wherein the divider comprises a curved shape.

6. The tracheal tube of claim 1, wherein the divider comprises a zigzag shape.

7. The tracheal tube of claim 1, wherein the divider is flexible.

8. The tracheal tube of claim 1, wherein an inner cross sectional dimension of the first ventilation lumen or the second ventilation lumen is at least 4 mm.

9. The tracheal tube of claim 1, wherein, at a portion of the first ventilation lumen not adjacent to the second ventilation lumen, the divider comprises a curved shape or semi-annular shape.

10. A tracheal tube, comprising:
a first ventilation lumen having a first distal end and a first proximal end, wherein the first lumen is coupled to a ventilator;
a second ventilation lumen adjacent to the first ventilation lumen, the second ventilation lumen having a second distal end and a second proximal end, wherein the second ventilation lumen is coupled to the ventilator;
an elastically deformable side wall, wherein the side wall forms at least a part of an exterior wall of the first ventilation lumen and the second ventilation lumen and extends to the second distal end; and
a divider disposed within the tracheal tube and dividing the first ventilation lumen from the second ventilation lumen, wherein the divider is more rigid than a portion of the side wall, such that the side wall deforms upon experiencing a biasing force to create an enlarged region when a medical device is introduced through the first ventilation lumen or the second ventilation lumen.

11. The tracheal tube of claim 10, wherein the divider is thicker than the elastically deformable side wall.

12. The tracheal tube of claim 11, wherein the divider is at least twice as thick as the elastically deformable side wall.

13. A tracheal tube, comprising:
a first ventilation lumen having a first distal end and a first proximal end;
a second ventilation lumen adjacent to the first ventilation lumen, the second ventilation lumen having a second distal end and a second proximal end, wherein the second distal end is not adjacent to the first distal end; and
a flexible divider disposed within the tracheal tube, the flexible divider dividing the first ventilation lumen from the second ventilation lumen and forming a portion of an exterior wall of the second ventilation lumen and wherein an annulus of the second ventilation lumen including the divider is formed from a same material wherein, without a biasing force, the divider creates substantially equal cross sectional areas in the first ventilation lumen and the second ventilation lumen, and wherein the flexible divider comprises alternating inelastic thick portion and elastomeric thin portions, and wherein the flexible divider is elastically deformable to create at least one enlarged region when a medical device is introduced through the enlarged region.

14. The tracheal tube of claim 13, wherein the thick portions and the thin portions are formed from the same material.

15. The tracheal tube of claim 14, wherein the thick portions and the thin portions are formed from the same material as the tracheal tube.

16. The tracheal tube of claim 13, wherein the flexible divider comprises an elastomeric membrane.

17. The tracheal tube of claim 13, wherein the first ventilation lumen or the second ventilation lumen has an inner diameter less than 4 mm without a biasing force applied to the flexible divider and wherein the flexible divider is adapted to stretch to provide an inner dimension suitable for introduction of the medial device of at least 4 mm in diameter.

* * * * *